(12) United States Patent
Brown et al.

(10) Patent No.: US 8,828,038 B2
(45) Date of Patent: Sep. 9, 2014

(54) LANCING DEVICE

(75) Inventors: Daniel Brown, Edwardsburg, MI (US); Martin Antoine Mathelier, Garnerville, NY (US); Maria Isabel Lorza, St. Augustine (CO); William McCloud, Pittsburgh, PA (US); Glenn Purcell, Edwardsburgh, MI (US); Tom Walker, Bristol (GB); Sehegeun Choi, Bristol (GB); Philip Walsh, Bristol (GB)

(73) Assignee: Bayer HealthCare LLC, Whippany, NJ (US)

( * ) Notice: Subject to any disclaimer, the term of this patent is extended or adjusted under 35 U.S.C. 154(b) by 132 days.

(21) Appl. No.: 12/995,806

(22) PCT Filed: Dec. 4, 2008

(86) PCT No.: PCT/US2008/013505
§ 371 (c)(1),
(2), (4) Date: Mar. 1, 2011

(87) PCT Pub. No.: WO2009/148431
PCT Pub. Date: Dec. 10, 2009

(65) Prior Publication Data
US 2011/0184448 A1    Jul. 28, 2011

Related U.S. Application Data

(63) Continuation-in-part of application No. 29/308,253, filed on Jun. 25, 2008, now Pat. No. Des. 616,987.

(60) Provisional application No. 61/131,138, filed on Jun. 6, 2008.

(51) Int. Cl.
*A61B 17/14* (2006.01)

(52) U.S. Cl.
USPC .......................................... 606/182; 600/583

(58) Field of Classification Search
USPC ................... 606/181, 182, 183; 600/573, 583
See application file for complete search history.

(56) References Cited

U.S. PATENT DOCUMENTS

| D342,573 S | 12/1993 | Cerola |
| 5,984,940 A | 11/1999 | Davis et al. |

(Continued)

FOREIGN PATENT DOCUMENTS

| KR | 30-0451541 | 6/2007 |
| KR | 30-0471097 | 12/2007 |

(Continued)

OTHER PUBLICATIONS

International Search Report, PCT/US2008/013505, dated Feb. 9, 2009.

(Continued)

*Primary Examiner* — Victor Nguyen
(74) *Attorney, Agent, or Firm* — Lerner, David, Littenberg, Krumholz & Mentlik, LLP

(57) ABSTRACT

A lancing device formed from a main body and a cap. The main body is configured from a lower housing, an upper housing extending over a portion of the lower housing, and an actuator operatively engaged to the upper and lower housings with the actuator extending along the portion of the lower housing not covered by the upper housing. The upper housing further includes an actuator button, wherein a lancet may be placed within the body such that movement of the actuator from a first position to a second position away from said endcap cocks the lancet for firing, which is achieved by depressing the actuator button. Conveniently, the lancing device is configured for tactile recognition in the palm of a human hand and may preferably be operated one handed and without visual observation.

15 Claims, 20 Drawing Sheets

(56) References Cited

U.S. PATENT DOCUMENTS

| | | |
|---|---|---|
| D428,150 S | 7/2000 | Ruf et al. |
| D444,557 S | 7/2001 | Levaughn et al. |
| 6,749,618 B2 * | 6/2004 | Levaughn et al. ............ 606/182 |
| D493,532 S | 7/2004 | Levaughn et al. |
| D523,555 S | 6/2006 | Loerwald et al. |
| D531,725 S | 11/2006 | Loerwald et al. |
| D550,363 S | 9/2007 | Hannant et al. |
| D560,805 S | 1/2008 | Young et al. |
| D569,975 S | 5/2008 | Wilkinson |
| D586,465 S | 2/2009 | Faulkner et al. |
| D586,916 S | 2/2009 | Faulkner et al. |
| 2007/0288047 A1 | 12/2007 | Thoes et al. |
| 2008/0039885 A1 | 2/2008 | Purcell |
| 2008/0058631 A1 | 3/2008 | Draudt et al. |

FOREIGN PATENT DOCUMENTS

| | | |
|---|---|---|
| TW | 425204 | 3/2001 |
| TW | D121165 | 1/2008 |
| TW | D122107 | 3/2008 |
| TW | D123459 | 5/2009 |
| WO | 2005/077275 A1 | 8/2005 |

OTHER PUBLICATIONS

Taiwan Utility Model No. TWM310692.

Taiwan Utility Model No. TWM310692—Translation.

English translation of the Decision of the Intellectual Property Office in Taiwan for Application No. 097147513 dated May 24, 2012.

Taiwan Design Reference No. D123459 dated Jun. 21, 2008.

Taiwan Office Action and Search Report for Application 097147513 dated Nov. 9, 2011.

Taiwan Search Report for Application No. 097306925 dated Jan. 5, 2010.

* cited by examiner

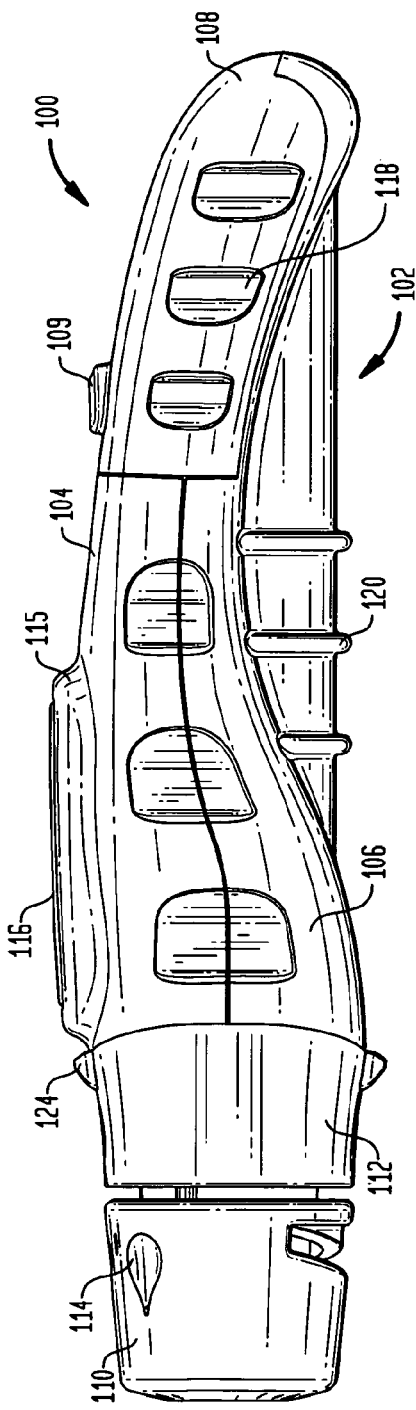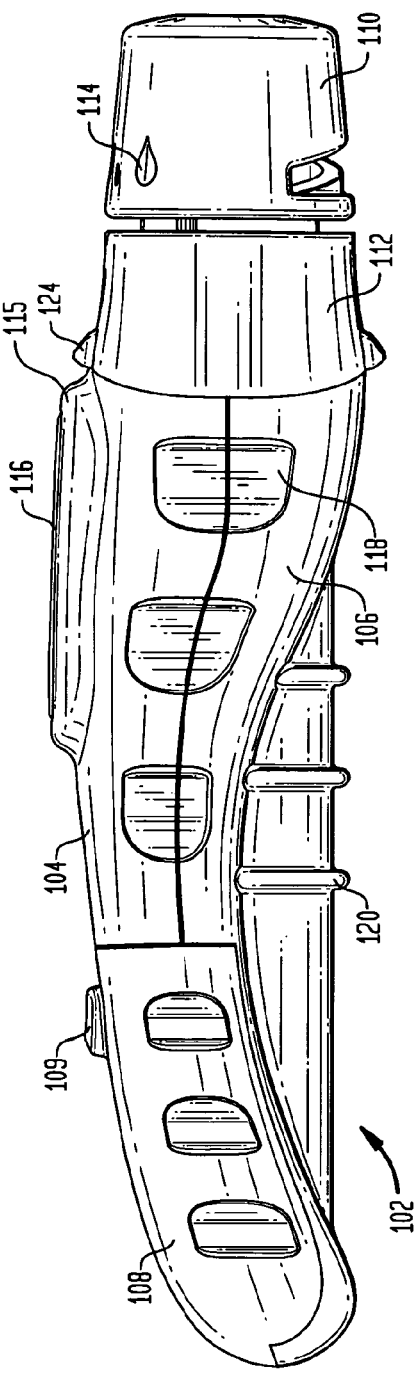

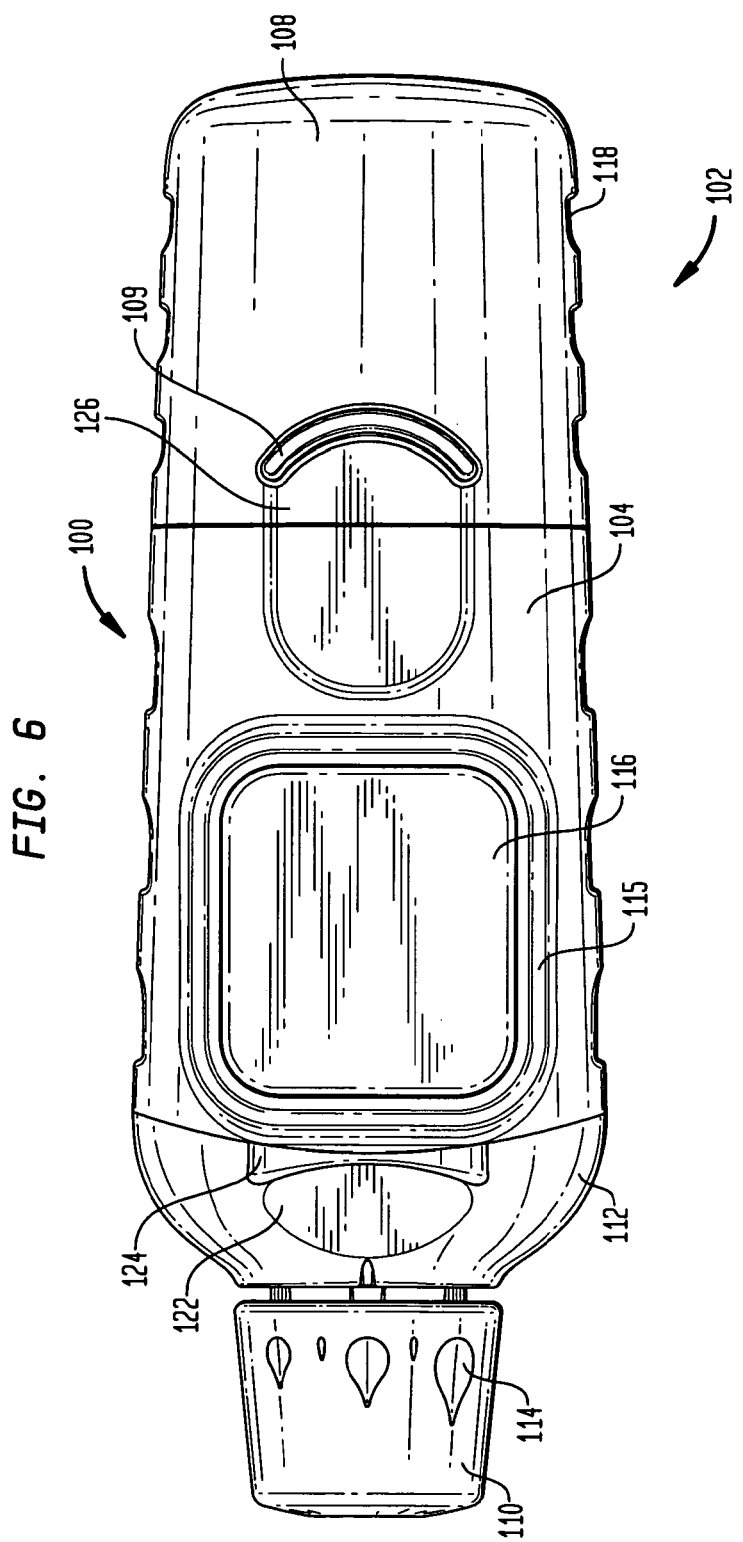

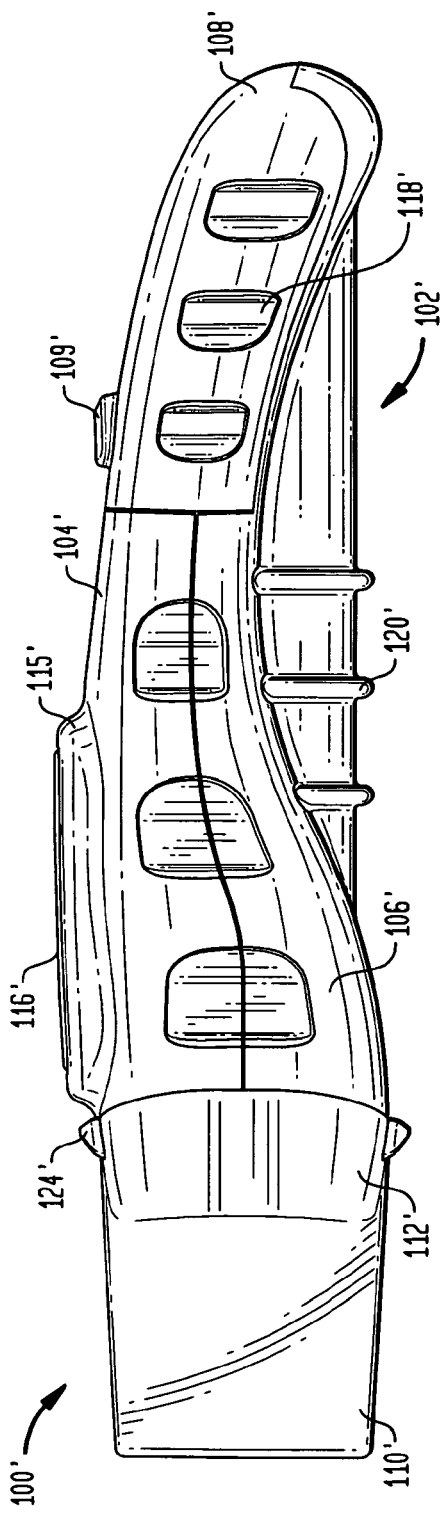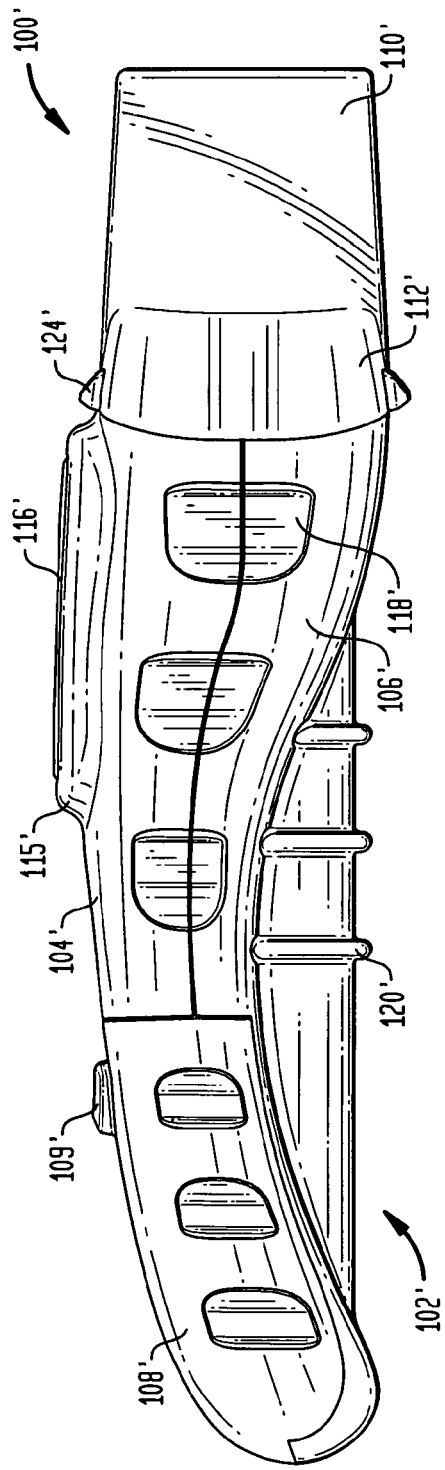

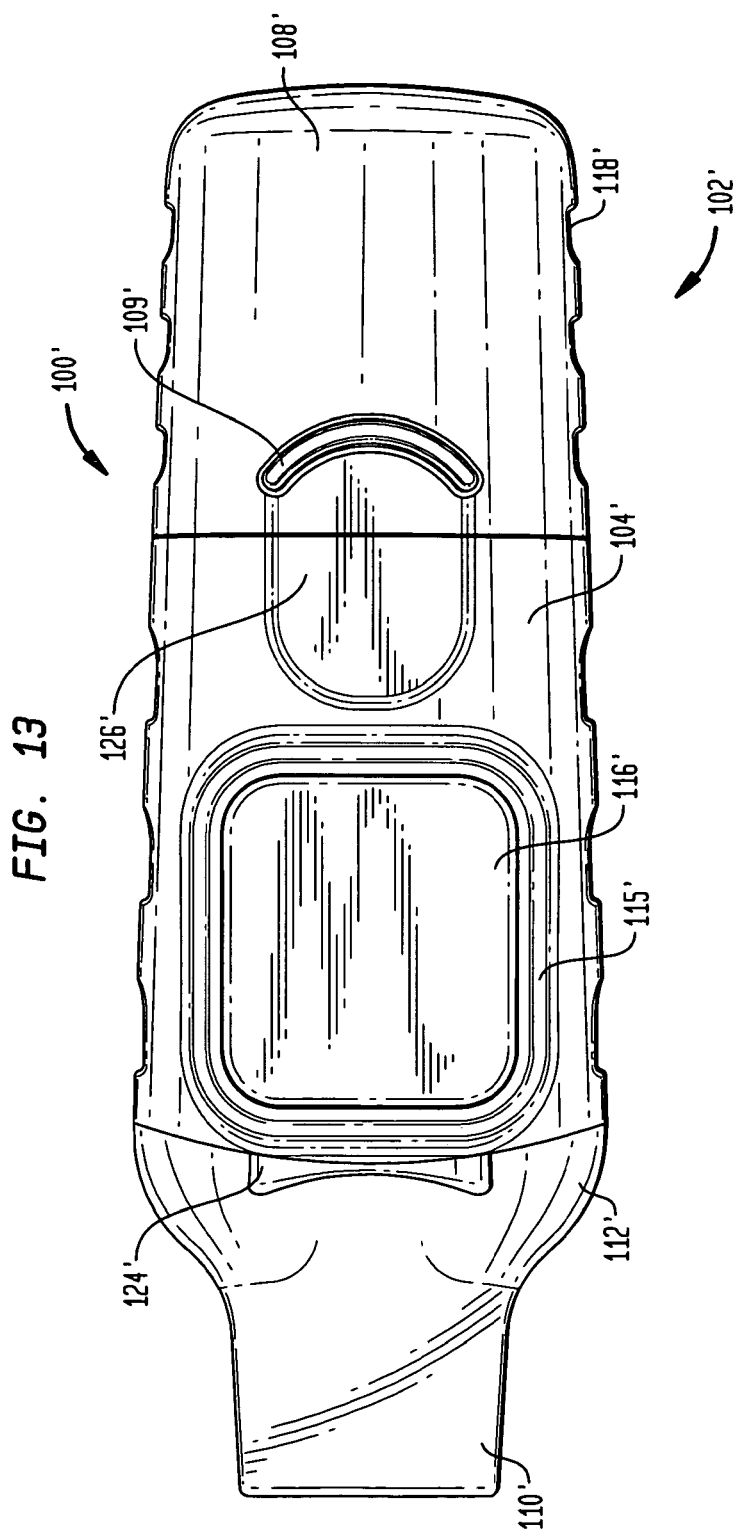

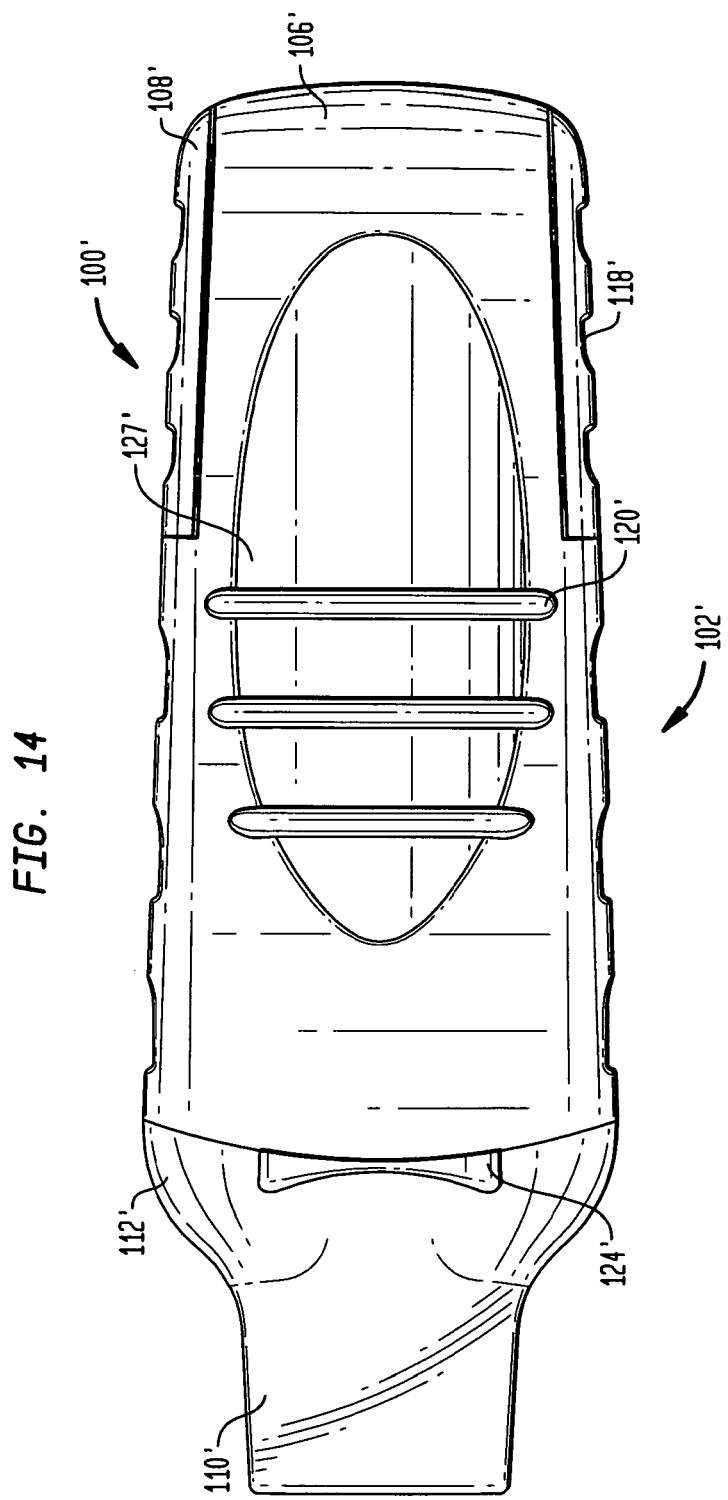

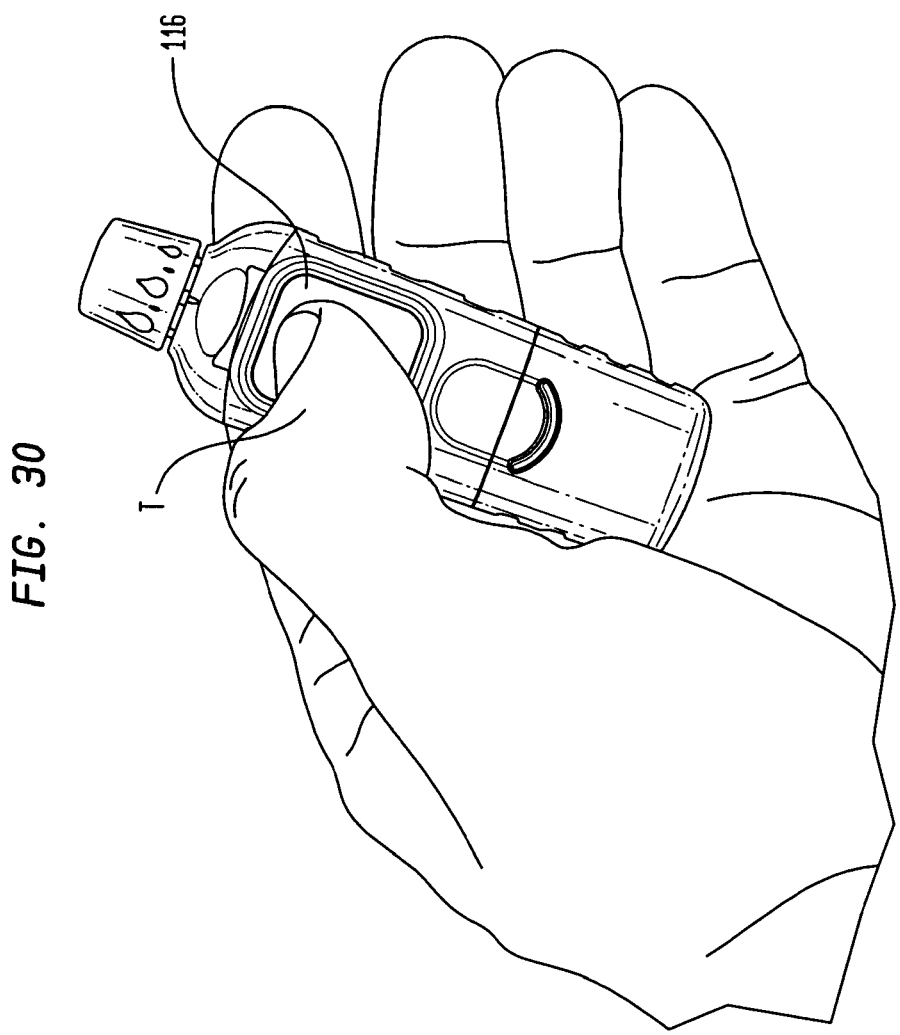

LANCING DEVICE

CROSS REFERENCE TO RELATED APPLICATIONS

This application is a 35 U.S.C. §371 National Stage Entry of PCT Application No. PCT/US2008/013505 filed Dec. 4, 2008 which is a continuation-in-part of U.S. patent application Ser. No. 29/308,253 filed Jun. 5, 2008 and which claims the benefit of the filing date of U.S. Provisional Patent Application No. 61/131,138 filed Jun. 6, 2008, the disclosure of which is hereby incorporated herein by reference.

TECHNICAL FIELD

This invention relates generally to devices utilized in the evaluation of glucose levels in patients with diabetes. More specifically, the present invention is directed toward improved lancing devices of the type utilized to pierce a patient's skin to produce a blood sample for glucose measurement. The lancing devices contemplated here are more ergonomic than prior devices (such as by being curved for orientation in the palm of a hand), which are predominantly pen-shaped, and therefore allow a previously unforeseen ease of use. This use extends to permitting one handed use through tactile manipulation, thus freeing the user's other hand and visual orientation for alternate endeavors.

BACKGROUND OF THE INVENTION

It is well known that individuals with diabetes may monitor their blood glucose levels several times per day. This is typically accomplished by piercing the skin with a lancet, most commonly in the area of a finger or forearm, and then placing a blood droplet from the piercing on a test strip which is then placed in a blood glucose monitor to establish a reading.

Most patients find it undesirable to pierce their own skin with a piercing device, so automatic lancing devices have become the norm. Heretofore, such devices have been cumbersome and not efficient. Predominantly, such devices have been pen-shaped, which can be cumbersome and not easily manipulated.

Difficult manipulation is particularly problematic when the diabetic is a child, an elderly person, someone with a handicap, or one with limited dexterity. It would therefore be beneficial to provide a lancing device that has improved implementation characteristics. For example, a lancing device which is operable with one hand would be most beneficial. In the case of a diabetic child, the caretaker could use one hand to gently orient the child while the lancet was operated with the other. Additionally, the free hand could assist with the milking process if needed. Preferably, the initial operation could be conducted without visually observing the lancing device, thus leaving the caretaker's visual orientation available for overseeing the child. For the elderly, a less cumbersome and more user friendly device has obvious advantages, particularly if the person also has impaired visibility and/or dexterity. Even with fully able bodied persons, an ergonomically better and functionally easier device would be welcome. The lancing devices of the present invention provide such.

SUMMARY OF THE INVENTION

In accordance with one aspect of the present invention, a lancing device may comprise a main body, the main body configured from a lower housing, an upper housing having an actuator button, the upper housing extending along a partial length of the lower housing, and an actuator operatively engaged to the upper and lower housings, the actuator extending along the remainder of the partial length of the lower housing. The lancing device may further comprise an endcap extending from the main body, where a lancet may be placed within the body such that movement of the actuator from a first position to a second position away from the endcap cocks the lancet for firing.

In such a lancing device, the actuator may be returned to the first position while the lancet remains cocked for firing.

In such a lancing device, the actuator button may be depressed to fire the cocked lancet.

In such a lancing device, the lancing device may fit in the palm of a typical adult hand.

In such a lancing device, the lancing device may be operated with one hand.

In such a lancing device, the upper housing and the lower housing may remain stationary when the actuator is moved from the first position to the second position.

In such a lancing device, the lower housing may be positioned against the forefinger of a typical adult hand while the actuator is moved with the thumb of a typical adult hand.

In such a lancing device, the actuator may extend beyond the limits of the lower housing when in the second position.

In such a lancing device, the actuator may further comprise a raised member to assist with movement thereof.

In accordance with another aspect of the present invention, a lancet device having a main body, an actuator, and an actuator button may deploy by grasping the main body of the lancet device with a single hand, positioning the lancet device such that the actuator faces away from the user's body, placing the thumb of a user on the actuator while the main body rests in the palm of the user, and moving the actuator from a first position to a second position to cock the lancet, whereby the main body remains stationary.

In such a method, the step of moving the actuator may be achieved with the user's thumb.

Such a method may further comprise rotating the lancet device within the palm such that the thumb of the person is above the actuator button.

Such a method may further comprise depressing the actuator button to fire the lancet.

Such a method may further comprise placing a lancet within the main body of the lancet device.

In such a method, the main body may comprise an upper portion and a lower portion, the lower portion sized and configured to mate directly with the upper portion and the actuator.

BRIEF DESCRIPTION OF THE DRAWINGS

The present invention will be readily understood by one skilled in the art by reviewing the following detailed description in conjunction with the accompanying drawings, wherein like reference numerals designate like structural elements, and in which:

FIG. 4 is a first side view of the lancing device of FIG. 1;

FIG. 5 is a second side view of the lancing device of FIG. 1;

FIG. 6 is a top view of the lancing device of FIG. 1;

FIG. 11 is a first side view of the lancing device of FIG. 8;

FIG. 12 is a second side view of-the lancing device of FIG. 8;

FIG. 13 is a top view of the lancing device of FIG. 8;

FIG. 14 is a bottom view of the lancing device of FIG. 8;

DETAILED DESCRIPTION OF THE INVENTION

The following description of the exemplary embodiments of the invention along with accompanying figures is presented by way of illustration and to facilitate an understanding of the invention by one of ordinary skill. The description is neither intended to be exhaustive nor meant to limit the scope of the invention in any manner. Accordingly, many modifications and variations are possible in the light of the disclosure.

Furthermore, the features and advantages described herein are not all-inclusive and, in particular, many additional features and advantages will be apparent to one of ordinary skill in the art in view of the drawings, specification, and claims. As will also be appreciated, the invention is capable of other and different embodiments, and its several details are capable of modifications in various respects without departing from the spirit and scope of the invention.

As discussed previously, it is contemplated that the lancing devices of the present invention incorporate features which make the devices more ergonomic and better functioning than prior lancing devices, which are predominantly pen-shaped. For example, the lancing device of the present invention is contemplated as being curved for orientation and tactical recognition in the palm of a human hand, therefore allowing a previously unforeseen ease of use such as one handed use and blind use. The lancing devices may also be loaded with lancets and cocked for delivery of the lancet in a convenient and efficient manner.

Figure 1:
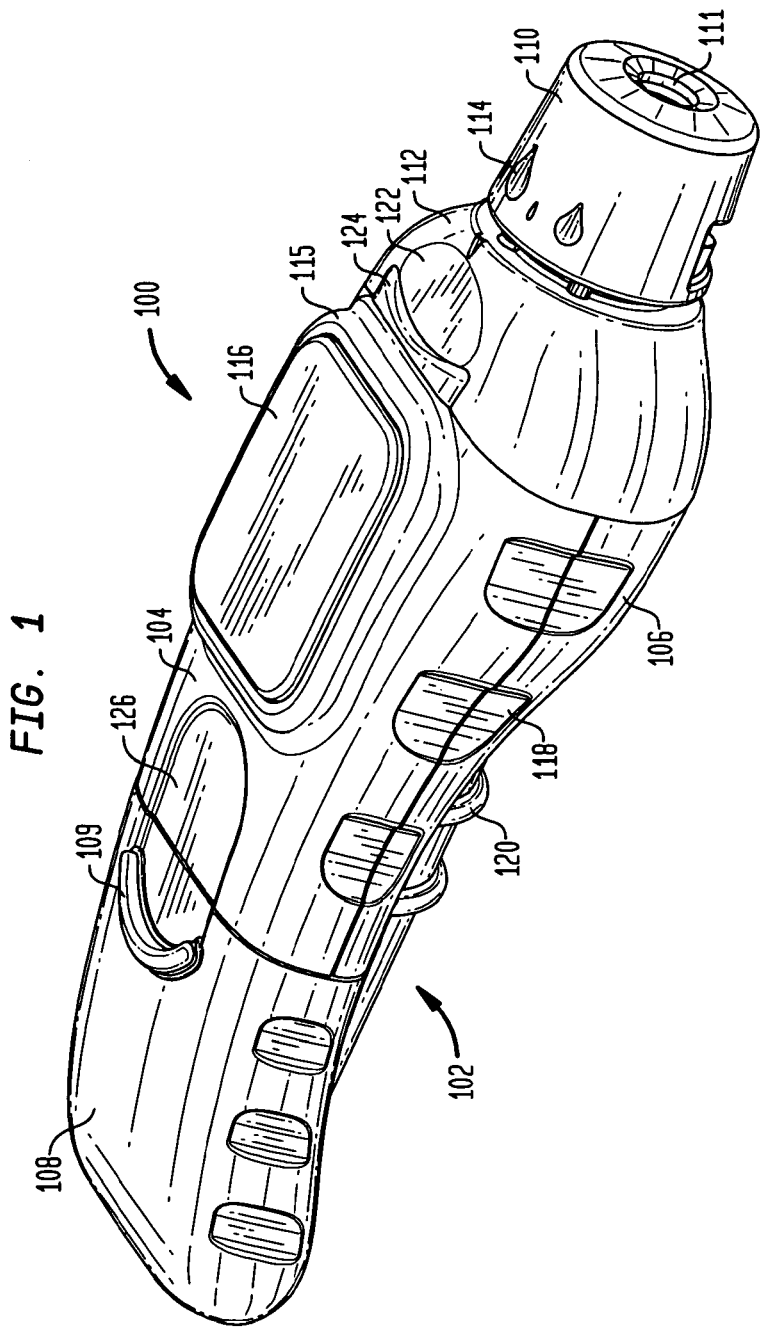
FIG. 1 is a perspective view of a lancing device in accordance with a first embodiment of the present invention, where the lancing device includes an adjustable endcap.

Referring to FIG. 1, a perspective view of a lancing device in accordance with a first embodiment of the present invention, it will be appreciated that the lancing device 100 may include a main body 102 configured from an upper portion 104, a lower portion 106 mated to the upper portion, and an actuator 108. The lancet device 100 may further include an endcap 110 mounted to the upper and lower portions 104, 106 by endcap shoulders 112.

The combination of upper portion 104 and actuator 108 are preferably configured to be of roughly the same length as the lower portion 106. As will be appreciated when discussing use of the device, this enables the lower portion 106 to be retained in stationary relation with the palm of a user's hand while the actuator 108 is moved away from the endcap 110 and then toward the endcap.

In the particular embodiment shown in FIG. 1, the endcap 110 is an adjustable endcap, whereby rotation of the endcap to the various positions indicated by the sized blood drops 114*a-c* (see FIG. 6 for full views) positions the distal end of endcap closer or further away from the main body 102. In the position rotated toward the smallest of the blood drops 114*c*, the endcap limits the excursion of a lancet placed within the lancing device such that the needle of the lancet penetrates the patient to a lesser degree than if the endcap were rotated toward the large blood drop, whereby the endcap would be positioned closest to the main body.

The lancet device 100 may also include an actuator button 116 disposed within the upper portion, depression of which is utilized to fire the lancet once the mechanism is cocked. Cocking of the device 100 may be achieved by first loading a lancet within the device, retracting the actuator 108 by pulling or pushing the actuator away from the upper portion 104, and then allowing the actuator to move back to the position shown in FIG. 1 directly adjacent the upper portion. It will be appreciated that springs may be provided to resist or assist with such movements.

Additional features of the lancet device 100 include a depression. 122 and associated tab 124 that are incorporated with the endcap 110, and more specifically the endcap shoulders 112. The depression 122 and tab 124 may be utilized to assist with removal of the endcap from the main body 102 of the lancet device by being suited for tactical and functional recognition by human fingers.

Figure 2:
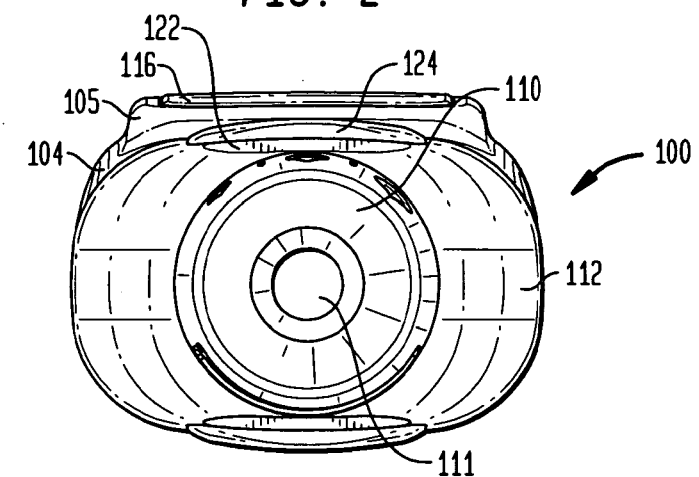
FIG. 2 is a frontal view of the lancing device of FIG. 1.
Figure 3:
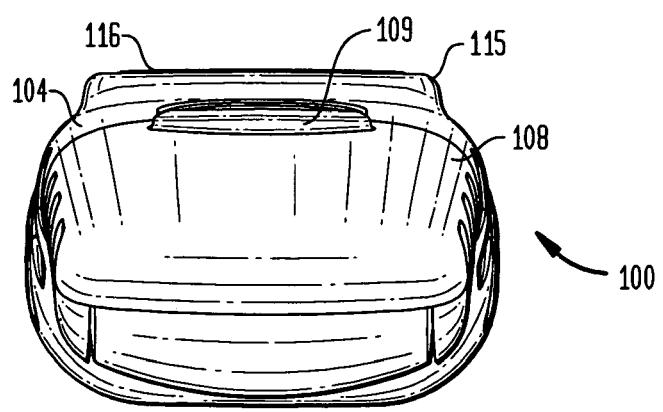
FIG. 3 is a rear view of the lancing device of FIG. 1.
Figure 7:
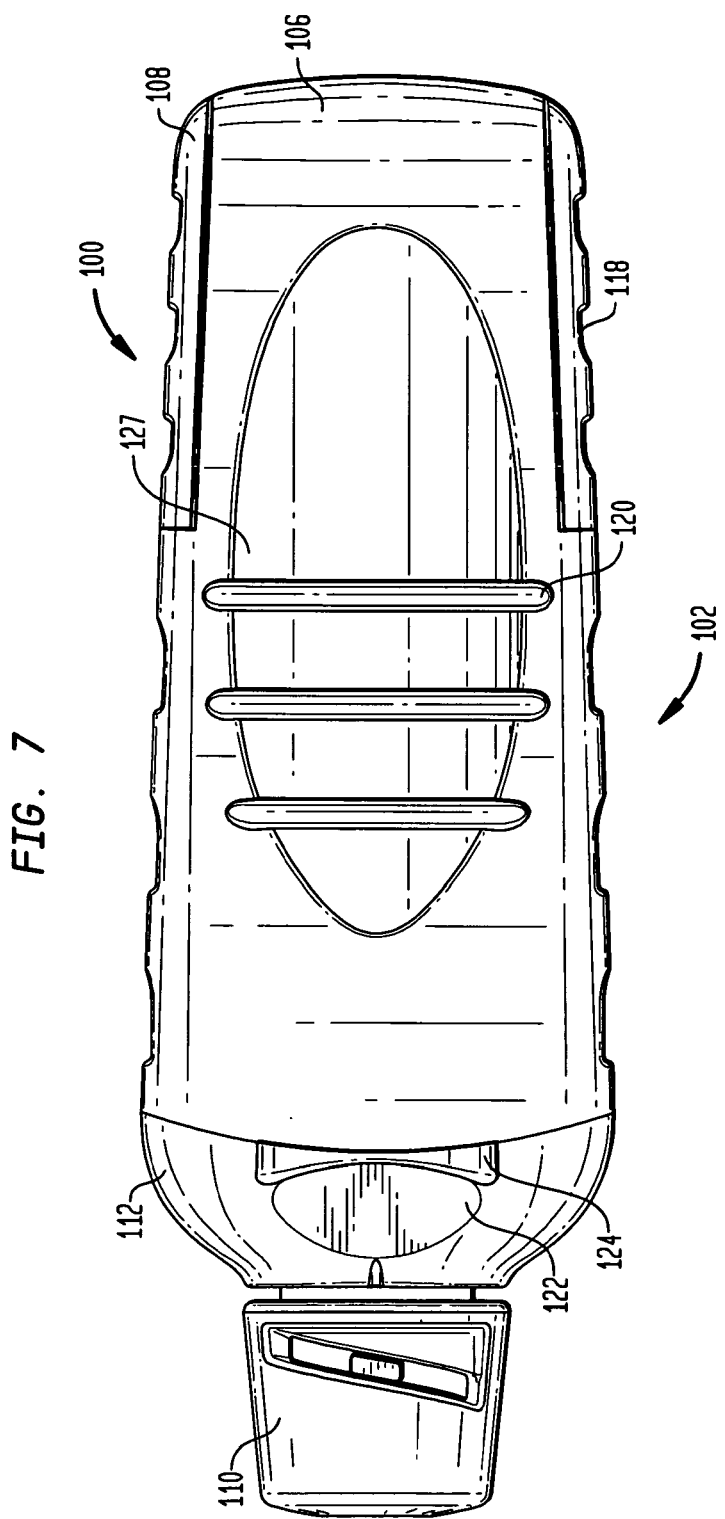
FIG. 7 is a bottom view of the lancing device of FIG. 1.
Figure 8:
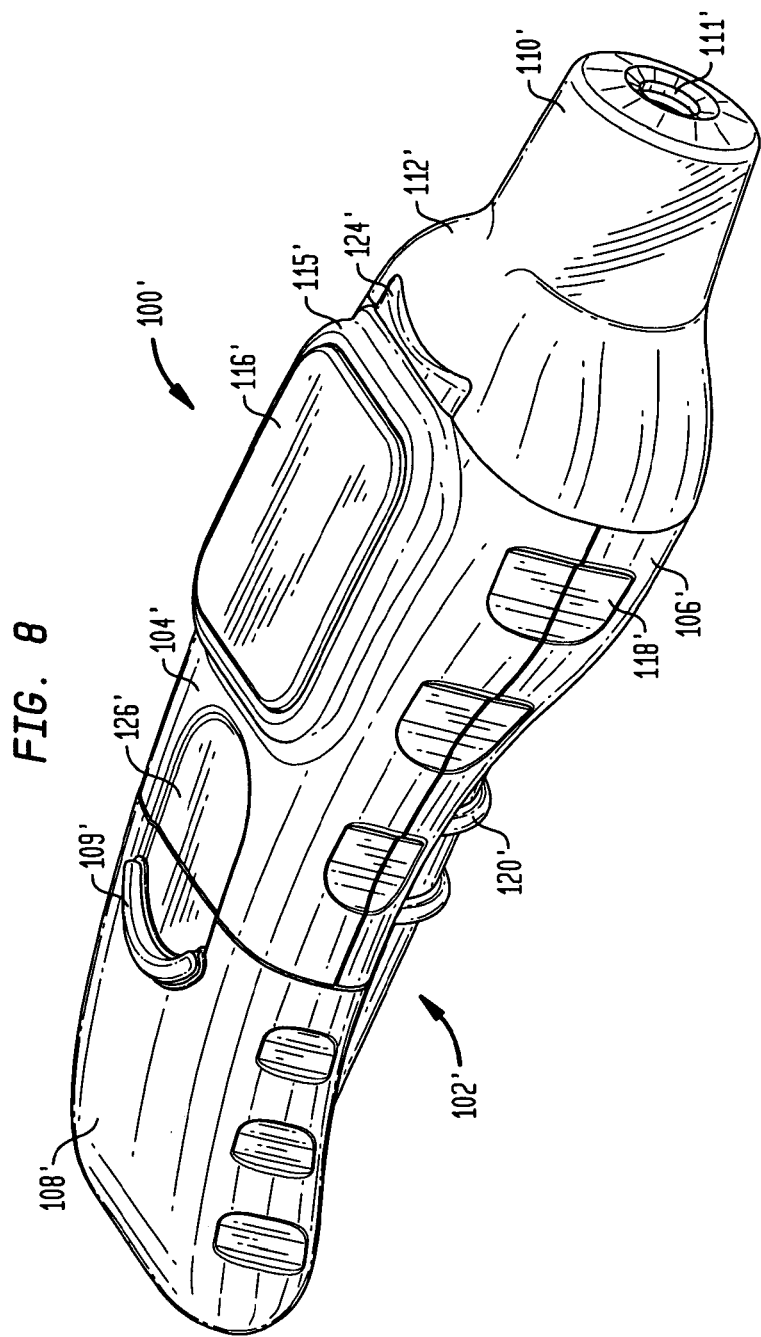
FIG. 8 is a perspective view of a lancing device in accordance with a second embodiment of the present invention, the embodiment differing from the first embodiment by the replacement of a non-adjustable cap in lieu of the adjustable cap depicted in the first embodiment.
Figure 9:
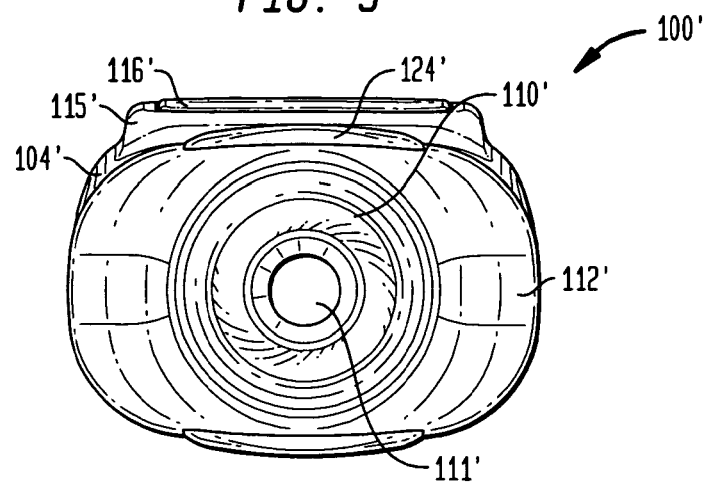
FIG. 9. is a frontal view of the lancing device of FIG. 8.
Figure 10:
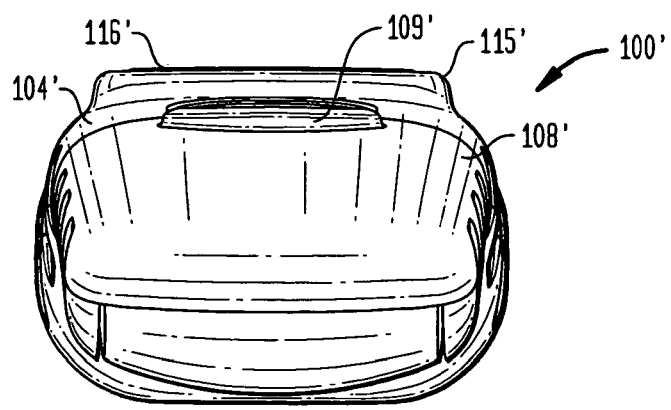
FIG. 10 is a rear view of the lancing device of FIG. 8.

FIGS. 2-7 depict additional views of the exemplary lancet device. Specifically, FIG. 2 depicts a frontal view of the exemplary lancing device, FIG. 3 depicts a rear view of the exemplary lancing device, FIG. 4 depicts a first side view of the exemplary lancing device, FIG. 5 depicts a second side view of the exemplary lancing device, FIG. 6 depicts a top view of the exemplary lancing device, and FIG. 7 depicts a bottom view of the exemplary lancing device.

In each of the views shown in FIGS. 2-7, like elements have been numbered with the equivalent reference numerals. For example, in FIG. 2 the front view depicts the endcap 110 in clear view. In this view, aperture 111, from which the needle of the lancet may penetrate, is clearly view. It will be appreciated that it is this aperture 111 which moves closer to or away from the main body 102 when the endcap 110 is rotated to permit deeper or shallower penetration of the lancet needle.

Moving briefly to a second embodiment of the lancing device, shown in FIGS. 8-14, it will be appreciated that the endcap 112' may be fixed, such that excursion of the lancet from within the device is similarly fixed. In this regard, the level of penetration into a patient is fixed. Moreover, the endcap is preferably substantially clear or translucent such that a user can view the lancet piercing the skin and may further manipulate the main body after piercing to enlarge the penetration. When sufficient blood is witnessed through the clear window, the user may then remove the lancet from the skin. In other embodiments the endcap may be provided as an opaque endcap.

The components previously listed, including the main body components and the two endcaps 112, 112', are preferably constructed from plastic. It will be appreciated that any of the components, particularly the endcaps 112, 112', may be configured from an antimicrobial plastic. Moreover, it is preferred that the upper and lower housings 104, 106 be one color while the actuator and actuator button 108, 116 are at least one other color to identify these moving components.

Figure 15:
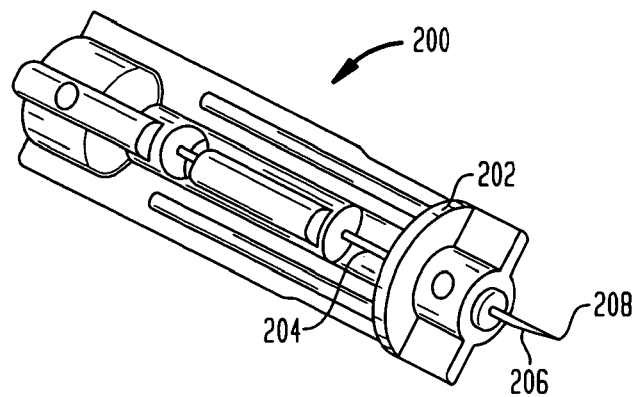
FIG. 15 is a perspective view of a lancet used with the lancing devices of the present invention.
Figure 16:
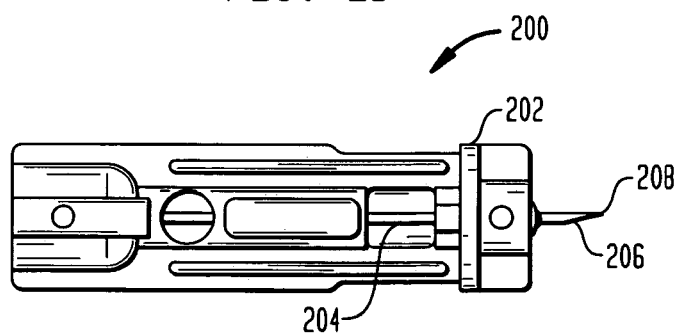
FIG. 16 is a top view of the lancet of FIG. 15.

Additional components of the lancing device 100 include a lancet 200, shown in FIGS. 15 and 16. Lancets such as lancet 200 are generally known in the art, and consists of a holder 202 and a needle 204 held within the holder. As is known, the needle 204 is fixed relative to the holder 202 and includes a distal end 206 which extends beyond the limits of the holder 202. It is this distal end 206 which is permitted to extend beyond the limits of the lancing device 100, includes the point 208, and penetrates the patient in use.

Figure 17:
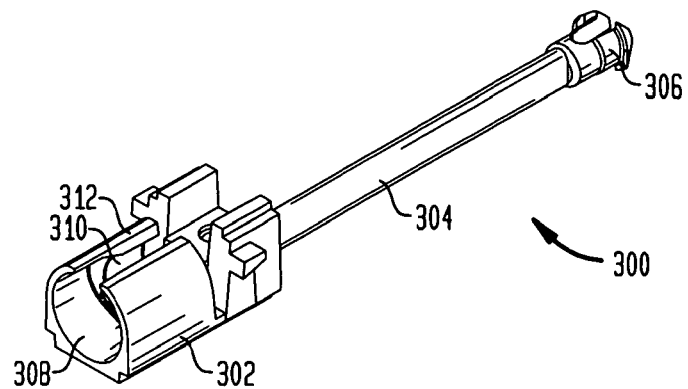
FIG. 17 is a top perspective view of the pusher forming a portion of the lancing devices of the present invention.
Figure 18:
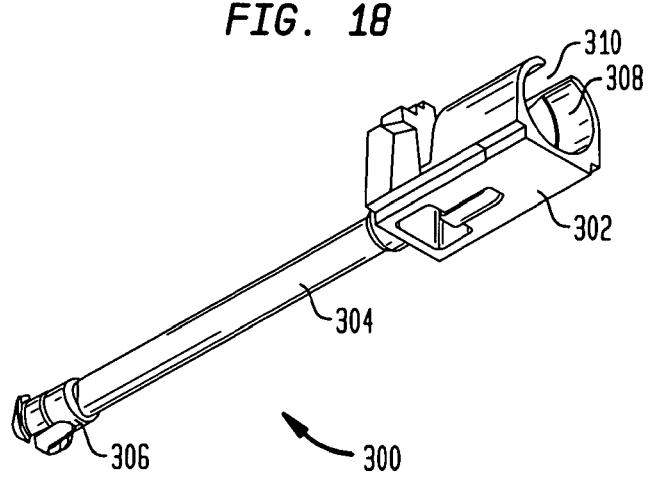
FIG. 18 is a bottom perspective view of the pusher of FIG. 17.
Figure 19:
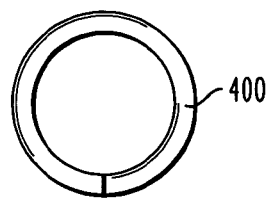
FIG. 19 is a frontal view of a first spring forming a portion of the lancing devices of the present invention.
Figure 21:
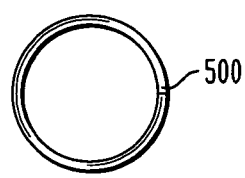
FIG. 21 is a frontal view a second spring forming a portion of the lancing devices of the present invention.
Figure 20:
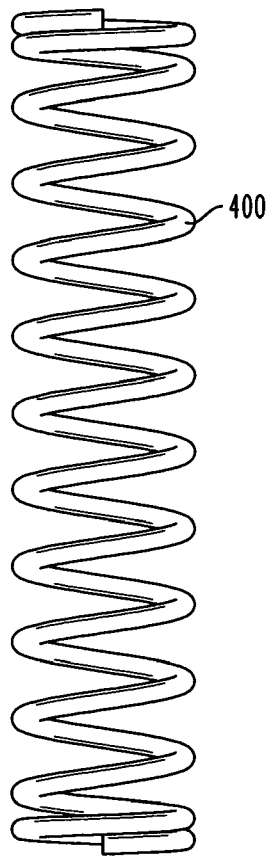
FIG. 20 is a side view of the first spring of FIG. 19.
Figure 22:
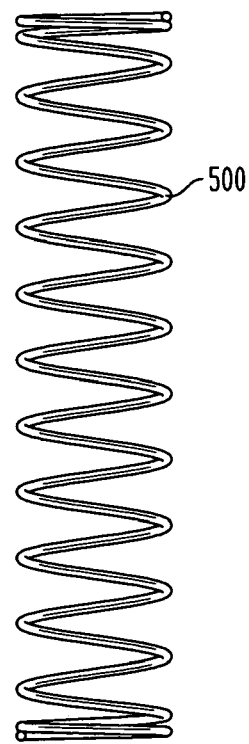
FIG. 22 is a side view of the second spring of FIG. 21.

Additional components include the pusher 300 shown in FIGS. 17 and 18 and the first spring 400 and second spring 500, the first spring being shown in FIGS. 19 and 20 and the second spring being shown in FIGS. 21 and 22.

The pusher 300 includes a holder 302 attached to a shaft 304 with a split head 306. It will be appreciated that the holder 302 is adapted to accept a lancet, such as lancet 200, within its cavity 308. Moreover, the cavity is formed from a split 310 within the holder 302 such that the holder may expand to retain the lancet 200 in a frictional relation. Lastly, the portion of the holder 302 forming the split 310 may include ramped portions 312 which provide progressive resistance against insertion of the lancet 200, or, stated another way, provides progressive ease of release of the lancet upon withdrawal from the holder 302.

As stated above, the springs 400, 500 are shown in FIGS. 19-22. Typically, the springs are made from any of the various metals known in the art and commonly used. Such springs may have the same or different spring rates, typically with the first spring 400 being formed to a higher rate than the second spring 500.

Figure 23:
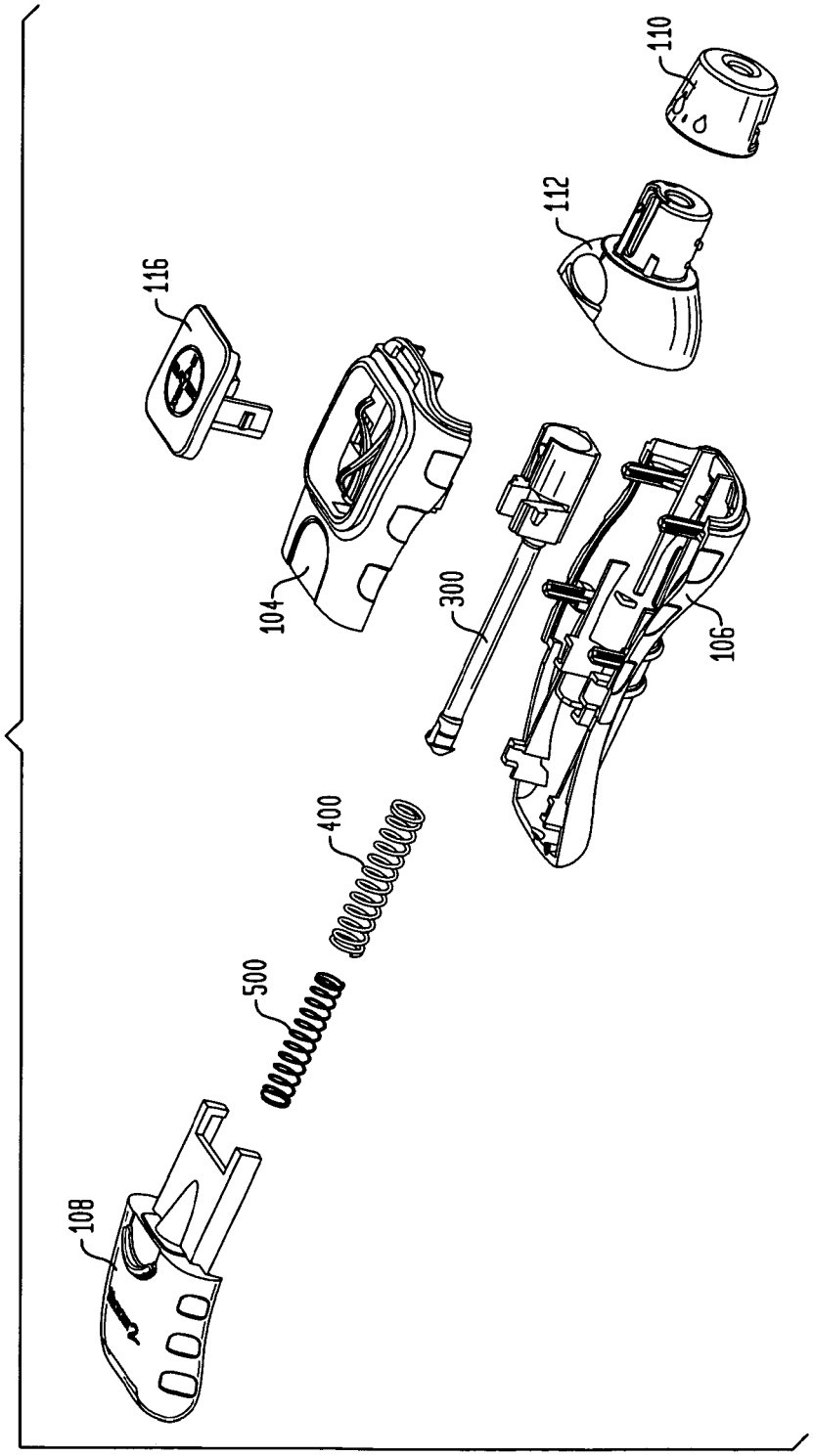
FIG. 23 is an exploded perspective view of the lancing device of FIG. 1.

FIG. 23 depicts an exploded view of the lancet device 100 of the first embodiment with the adjustable endcap. As such, shown is the upper-portion 104, lower portion 106, actuator 108, endcap 110, endcap shoulders 112, button 116, pusher 300, and lastly springs 400, 500. It will be appreciated that each of the elements include mating members, such as tabs, pins, and associated mating recesses for connection with the intended adjacent member. Such mating members are well known in the art.

Figure 24:
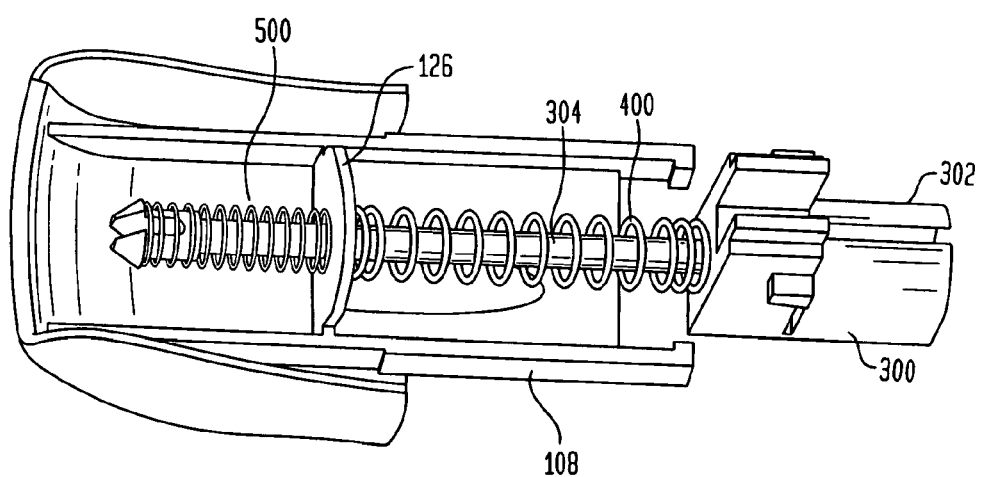
FIG. 24 is an internal view of a portion of the lancing device of FIG. 1.

Operation of the lancing device 100 will be better understood upon evaluation of FIG. 24, a bottom view of the actuator 108 together with the holder 300 and springs 400, 500 installed. It will be appreciated that the springs 400, 500 are threaded onto the shaft 304 of the pusher 300 with the first spring nearest the holder 308 and the second spring nearest the split head 306. In the meantime, the actuator 108 includes a partition wall 126 on its interior, the partition wall including an aperture (not shown). The pusher 300 and spring 400, 500 arrangement is arranged such that the split head 306 and second spring 500 are on one side of the partition wall 126 while the holder 308 and first spring 400 are on the other, the shaft 304 penetrating through the aperture of the partition wall.

Figure 25:
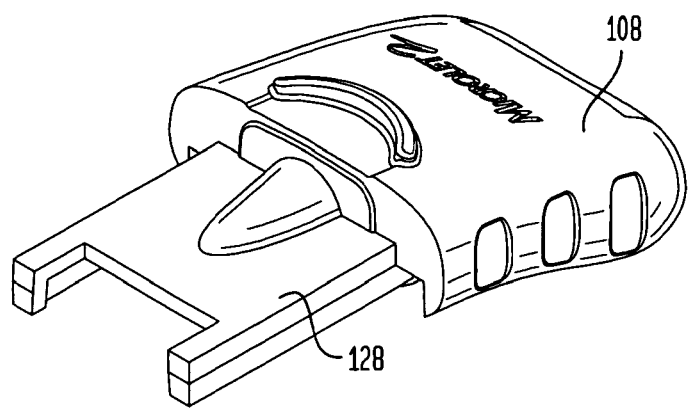
FIG. 25 is a top perspective view of an actuator forming a portion of certain lancing devices of the present invention.
Figure 26:
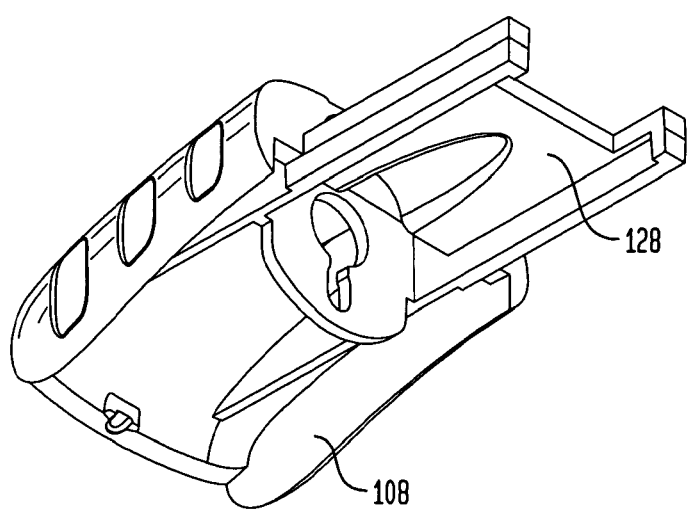
FIG. 26 is a bottom perspective view the actuator of FIG. 25.

Additional views of the actuator 108 are shown in FIGS. 25 and 26. It will be appreciated that the actuator 108 also includes a slide member 128 extending beyond the portion of the actuator in view in FIG. 1. The slide penetrates into the combination of the upper housing 104 and lower housing 106 in retained relation, such that the actuator may be withdrawn from the combination of upper housing 104 and lower housing 106. Such withdrawal compresses the first spring 500 and second spring 500. Upon release of the actuator, the compression of the second spring 500 releases, but compression of the first spring 400 remains such that the lancing device 100 is cocked for firing. This cocking action is achieved by action of the holder 302 being retained by the button 116. Upon depressing of the button 116, the holder 302 is released and the needle portion of the lancet 200, previously placed within the holder 302, is forced through the aperture 111 of the endcap 110 to penetrate the skin of a patient.

Moving to FIGS. 27-30, the method of using the lancing device 100 will be discussed in additional detail.

It is assumed for purposes herein that the lancing device is preloaded with a lancet 200 as known in the art.

Figure 27:
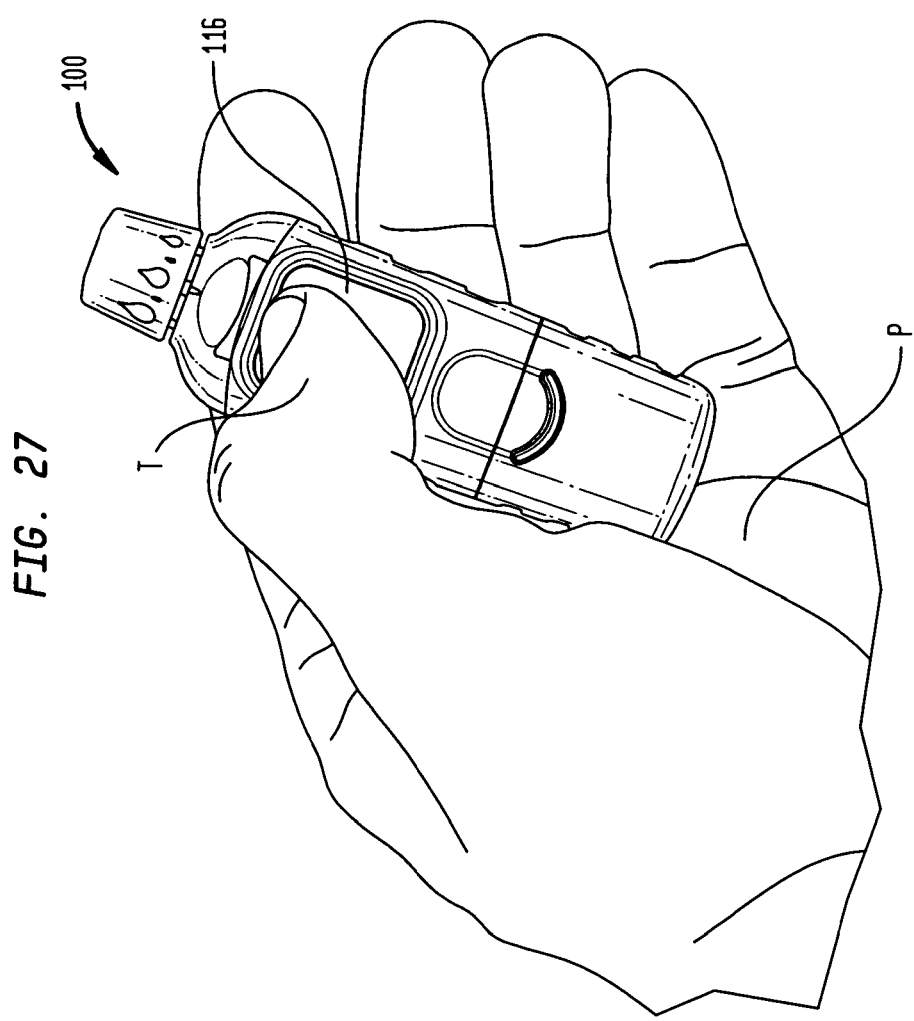
FIG. 27 is a perspective view of a first step in the use of the lancing devices of the present invention.

The first step in such method is for the user to grasp the device 100 as shown in FIG. 27. Although shown with the user's thumb (T) over the actuation button 116, such position is not necessary. Rather, the user may simply grasp the device 100 in the users palm (P). Of note is the curved ergonomic shape of the device 100, including the side scallops 118 and lower ribs 120, which aid in grasping and orienting of the device.

Figure 28:
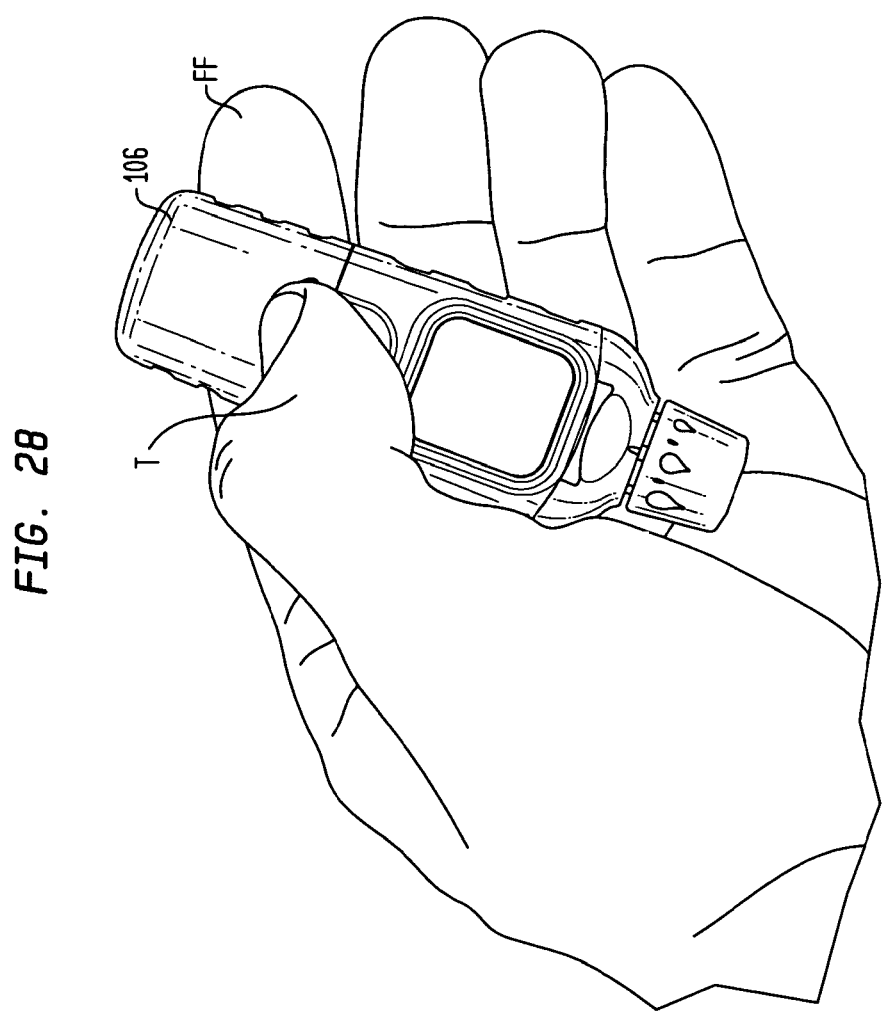
FIG. 28 is a perspective view of a second step in the use of the lancing devices of the present invention.
Figure 29:
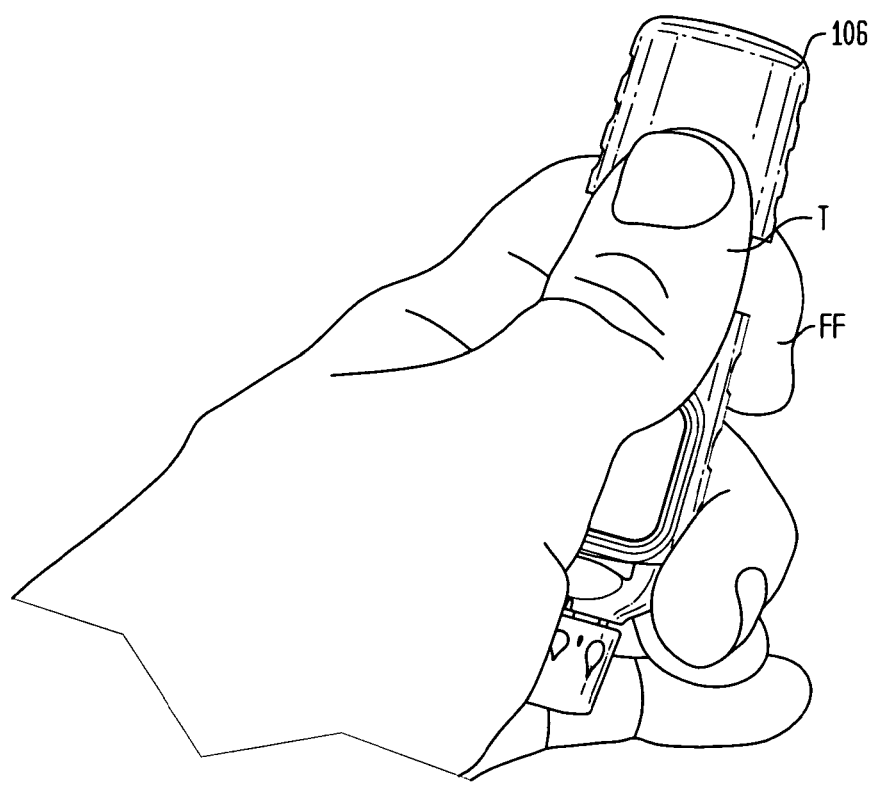
FIG. 29 is a perspective view of a third step in the use of the lancing devices of the present invention; and, FIG. 30 is a perspective view of a fourth step in the use of the lancing devices of the present invention.

From the standard position shown in FIG. 27, the user may rotate the device 100 within his palm (P) such that the actuator 108 faces away from the body, as shown in FIG. 28. From this position, the user may easily move the actuator 108 from the position shown in FIG. 28 to the extended position shown in FIG. 29, away from the endcap 110. To aid in such movement, the actuator 108 may include a raised portion 109. This serves to cock the lancet 200 for delivery, as previously discussed. It will also be appreciated that such procedure may readily be accomplished with one hand. One feature of the device 100 in this regard is that the device is sized and configured such that the forefinger (FF) of the user may rest upon the lower housing 106, as shown in FIG. 28. In this position, the lower housing 106 is stationary relative to the user's body and remainder of the main body 102 of the device as the actuator 106 is moved from the position of FIG. 28 to the extended position of FIG. 29.

Following such procedure, the device 100 may again be rotated back to the original position, as shown in FIG. 30 whereupon a user may use his thumb (T) to depress the actuation button 116 to fire the lancet 200. In this regard, it will be appreciated that the lancet 200 is fired from the distal end of the endcap 110, through the aperture 111, and into the skin of a patient, which may or may not be the user.

After firing, the endcap 110 and shoulders 112 may be removed from the device 100 to expose the used lancet 200, whereupon the lancet may be removed from the holder 302 and discarded. To aid in installation of a lancet 200 and subsequent removal thereof, the holder 302 may be constructed in a split configuration, as discussed above, such that the holder 302 may flex and retain the lancet in a frictional relation. In addition, the holder 302 may include ramped portions 312 to aid in insertion, retention, and removal of the lancet 200, the lancet 200 using the ramped portions 312 to force open the holder 302.

Although, this invention has been described particularly in relation to the lancing devices disclosed, it will be recognized that the features and benefits of the overall construction described herein are applicable to other articles. Also, it would be realized by those skilled in the art that various modifications, alterations and adaptations can be made to this invention without departing from the spirit and scope of this invention. Numerous characteristics and advantages have been set forth in the foregoing description, together with details of structures and functions of the present invention. The foregoing description and disclosure, however, is illustrative only, and change may be made in arrangement and details, within the principle of the invention to the full extent indicated by the broad general meaning of the terms in which the appended claims are expressed.

Industrial Applicability

The present invention has applicability in the field of medical devices.

The invention claimed is:

1. A lancing device comprising:
   a main body, the main body configured from a lower housing, an upper housing having an actuator button, the upper housing extending along a partial length of the lower housing, and an actuator operatively engaged to said upper and lower housings, the actuator extending along the remainder of the partial length of said lower housing; and
   an endcap extending from said main body;
   wherein the lower housing has a first end adjacent the end cap and an opposed second end underlying the actuator;
   wherein the lower housing has a curved profile along a length of the device between the first and second ends;
   wherein a lancet may be placed within said body such that movement of said actuator from a first position to a second position away from said endcap cocks the lancet for firing, and
   wherein said lancing device is constructed and arranged such that it is capable of being actuated with one hand while being held by the one hand.

2. The lancing device of claim 1, wherein said actuator may be returned to said first position while the lancet remains cocked for firing.

3. The lancing device of claim 1, wherein said actuator button is depressed to fire said cocked lancet.

4. The lancing device of claim 1, wherein said lancing device fits in a palm of a typical adult hand.

5. The lancing device of claim 4, wherein the lancing device can be operated while in a palm of the one hand.

6. The lancing device of claim 1, wherein said lancing device can be operated with the one hand.

7. The lancing device of claim 1, wherein said upper housing and said lower housing remain stationary when said actuator is moved from said first position to said second position.

8. The lancing device of claim 7, wherein said lower housing may be positioned against the forefinger of a typical adult hand while the actuator is moved with the thumb of a typical adult hand.

9. The lancing device of claim 1, wherein the actuator extends beyond the limits of the lower housing when in said second position.

10. The lancing device of claim 1, wherein said actuator further comprises a raised member to assist with movement thereof.

11. The lancing device of claim 1, further comprising a holder within the main body, the holder adapted to accept and hold a lancet, the holder including ramped portions providing progressive resistance against the lancet during insertion and removal.

12. A lancing device comprising:
    a main body, said main body configured from a lower housing and an upper housing having an actuator button, and an actuator slidably engaged to said upper and lower housings; and
    an endcap extending from said main body;
    wherein a combined length of the upper housing and the actuator is substantially equal to a length of the lower housing,
    wherein the lower housing has a first end adjacent the end cap and an opposed second end underlying the actuator;
    wherein the lower housing has a curved profile along a length of the device between the first and second ends;
    wherein a lancet may be placed within said body such that movement of said actuator from a first position to a second position away from said first upper housing cocks said lancet for firing, and
    wherein said lancing device is constructed and arranged such that it is capable of being actuated with one hand while being held by the one hand.

13. The lancing device of claim 12, wherein said actuator may be returned to said first position while said lancet remains cocked for firing.

14. The lancing device of claim 12, wherein said actuator button is depressed to fire said cocked lancet.

15. The lancing device of claim 12, wherein said lancing device is constructed and arranged to fit within a palm of a typical adult hand.

* * * * *

UNITED STATES PATENT AND TRADEMARK OFFICE
CERTIFICATE OF CORRECTION

PATENT NO. : 8,828,038 B2  
APPLICATION NO. : 12/995806  
DATED : September 9, 2014  
INVENTOR(S) : Daniel Brown et al.

Page 1 of 1

It is certified that error appears in the above-identified patent and that said Letters Patent is hereby corrected as shown below:

ON THE TITLE PAGE

Item (75), under "Inventors", in Column 1, Line 6, delete "Edwardsburgh," and insert -- Edwardsburg, --, therefor.

IN THE SPECIFICATION

In Column 5, Line 59, delete "holder 300" and insert -- holder 302 --, therefor.

Signed and Sealed this  
Fourteenth Day of April, 2015

Michelle K. Lee  
*Director of the United States Patent and Trademark Office*

UNITED STATES PATENT AND TRADEMARK OFFICE
CERTIFICATE OF CORRECTION

| | | |
|---|---|---|
| PATENT NO. | : 8,828,038 B2 | Page 1 of 1 |
| APPLICATION NO. | : 12/995806 | |
| DATED | : September 9, 2014 | |
| INVENTOR(S) | : Brown et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this
Twenty-ninth Day of September, 2015

Michelle K. Lee
*Director of the United States Patent and Trademark Office*